(12) United States Patent
Akad

(10) Patent No.: US 10,132,100 B1
(45) Date of Patent: Nov. 20, 2018

(54) SNOW REMOVAL MATTRESS

(71) Applicant: Aharon Akad, Fair Lawn, NJ (US)

(72) Inventor: Aharon Akad, Fair Lawn, NJ (US)

(73) Assignee: Aharon Akad, Fair Lawn, NJ (US)

( * ) Notice: Subject to any disclaimer, the term of this patent is extended or adjusted under 35 U.S.C. 154(b) by 0 days.

(21) Appl. No.: 15/928,192

(22) Filed: Mar. 22, 2018

Related U.S. Application Data

(63) Continuation-in-part of application No. 15/696,253, filed on Sep. 6, 2017.

(51) Int. Cl.
| | | |
|---|---|---|
| *E04H 15/20* | (2006.01) | |
| *A61F 7/00* | (2006.01) | |
| *E01C 11/26* | (2006.01) | |
| *E04D 13/10* | (2006.01) | |
| *E01H 5/10* | (2006.01) | |
| *E01C 11/24* | (2006.01) | |

(52) U.S. Cl.
CPC .......... *E04H 15/20* (2013.01); *A61F 7/0097* (2013.01); *E01C 11/24* (2013.01); *E01C 11/26* (2013.01); *E01H 5/10* (2013.01); *E01H 5/102* (2013.01); *E04D 13/106* (2013.01); *E04H 2015/202* (2013.01); *E04H 2015/203* (2013.01); *E04H 2015/205* (2013.01); *E04H 2015/206* (2013.01); *E04H 2015/208* (2013.01)

(58) Field of Classification Search
None
See application file for complete search history.

(56) References Cited

U.S. PATENT DOCUMENTS

| | | | | |
|---|---|---|---|---|
| 2,830,606 A | * | 4/1958 | Daugherty | E04H 15/20 119/436 |
| 3,463,174 A | | 8/1969 | Heller | |
| 4,160,523 A | * | 7/1979 | Stevens | A01G 9/243 126/625 |
| 4,936,060 A | * | 6/1990 | Gelinas | E04D 13/103 52/1 |
| 5,405,371 A | * | 4/1995 | Augustine | A47G 9/0215 607/107 |
| 5,579,796 A | | 12/1996 | Mallo et al. | |
| 6,730,115 B1 | * | 5/2004 | Heaton | A47C 21/044 5/421 |
| 7,880,121 B2 | | 2/2011 | Naylor | |

(Continued)

FOREIGN PATENT DOCUMENTS

| CA | 2079947 A | * | 4/1994 |
|---|---|---|---|
| CA | 2851697 A1 | * | 11/2015 |

(Continued)

*Primary Examiner* — Robert Canfield
(74) *Attorney, Agent, or Firm* — Gearhart Law LLC

(57) ABSTRACT

An inflatable air mattress for preventing snow accumulation is provided. The mattress comprises an inflatable portion comprising a textile material, and an outside air intake. A fan draws outside air into the inflatable portion through the air intake, and circulates the air when inflated. An air divider alternates between an inflating position and a circulating position that determines which air the fan blows. An air heater heats the air that passes through the fan. A controller activates the fan and air heater based on a signal from a snow sensor; controls the divider based on a signal from a pressure sensor; and controls the heater based on a signal from a heat sensor.

20 Claims, 19 Drawing Sheets

(56) References Cited

U.S. PATENT DOCUMENTS

| | | | |
|---|---|---|---|
| 8,997,769 | B2 | 4/2015 | Carpenter |
| 9,004,088 | B1 | 4/2015 | Nicheporuck |
| 9,271,416 | B2 | 2/2016 | Carpenter |
| 2003/0121539 | A1 | 7/2003 | Gu |
| 2004/0021575 | A1* | 2/2004 | Oskorep ................. B60S 1/026 340/601 |
| 2004/0187216 | A1* | 9/2004 | Lin ...................... A47C 21/048 5/706 |
| 2005/0254802 | A1* | 11/2005 | Shields ................... E01C 11/26 392/379 |
| 2010/0176118 | A1 | 7/2010 | Lee et al. |
| 2010/0200035 | A1 | 8/2010 | Jordache et al. |
| 2011/0035880 | A1* | 2/2011 | Cole ................... A47C 27/082 5/423 |
| 2014/0196210 | A1* | 7/2014 | Lachenbruch ......... A61G 7/001 5/423 |
| 2015/0211282 | A1 | 7/2015 | Potvin |
| 2015/0282631 | A1* | 10/2015 | Creamer .............. A47C 21/044 5/423 |
| 2016/0100457 | A1* | 4/2016 | Cole ........................ H05B 3/36 219/213 |
| 2016/0369466 | A1* | 12/2016 | Chi-Hsueh ................ E01H 5/10 |
| 2017/0335523 | A1* | 11/2017 | Moussa ................. E01C 11/265 |

FOREIGN PATENT DOCUMENTS

| | | | | |
|---|---|---|---|---|
| FR | 2727144 | A1 * | 5/1996 | ................ E01F 7/04 |
| GB | 2065465 | A * | 7/1981 | ........... A47C 21/048 |
| JP | 2000055480 | A * | 2/2000 | |
| JP | 2000220321 | A * | 8/2000 | |

* cited by examiner

SNOW REMOVAL MATTRESS

This application is a Continuation In Part of U.S. application Ser. No. 15/696,253, filed Sep. 6, 2017, the entire contents of which are incorporated herein.

FIELD OF THE EMBODIMENTS

The field of embodiments of this invention relates to air mattresses adapted for snow removal.

BACKGROUND OF THE EMBODIMENTS

Within the United States, 35 of the 50 states receive on average, at least two feet of snow per year. Snow can create hazards of slippery walks and driveways. Thus, clearing snow is a common occurrence during winter months in a majority of states with in the United States. Shoveling, even pushing a heavy snow blower, can cause sudden increase in blood pressure and heart rate, and the cold air can cause constriction of blood vessels and decrease oxygen to the heart. Thus, heart attacks become more of a risk during strenuous snow-clearing because blood pressure and heart rates spike while cold air constricts blood vessels and decreases the amount of oxygen received by the heart. When these factors combine and a person is not in peak health, shoveling can be a deadly activity.

SUMMARY OF THE EMBODIMENTS

An inflatable air mattress for preventing snow accumulation is provided. The mattress comprises an inflatable portion comprising a textile material, and an outside air intake. A fan draws outside air into the inflatable portion through the air intake, and circulates the air when inflated. An air divider alternates between an inflating position and a circulating position that determines which air the fan blows. An air heater heats the air that passes through the fan. A controller activates the fan and air heater based on a signal from a snow sensor; controls the divider based on a signal from a pressure sensor; and controls the heater based on a signal from a heat sensor.

It is to be understood that both the foregoing general description and the following detailed description are exemplary and explanatory and are intended to provide further explanation of the invention as claimed.

BRIEF DESCRIPTION OF THE DRAWINGS

The structure, operation, and advantages of disclosed embodiments will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity.

DESCRIPTION OF THE PREFERRED EMBODIMENTS

Figure 1A:
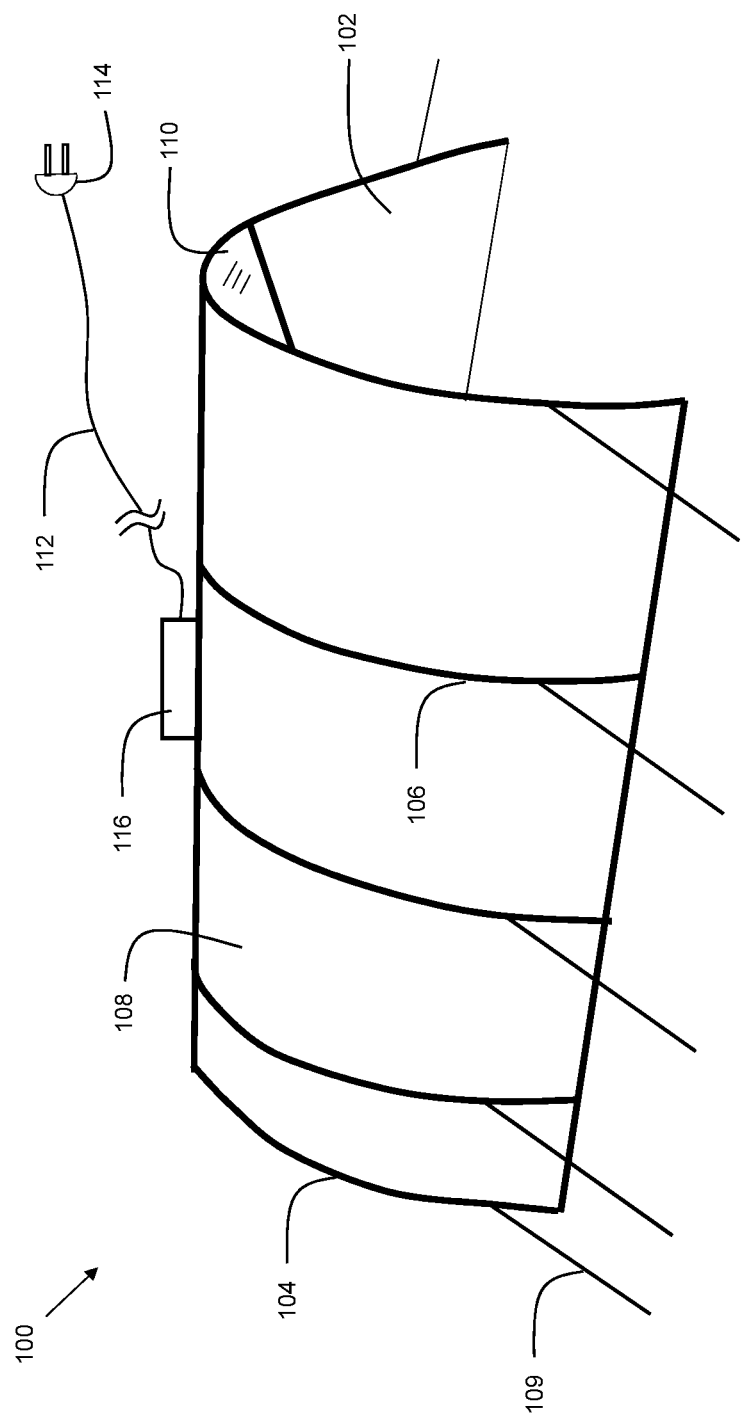
FIG. 1A shows a snow removal tent in accordance with embodiments of the present invention.

FIG. 1A shows a snow removal tent 100 in accordance with embodiments of the present invention. Tent 100 includes a textile material 108 supported by a plurality of supports 106. In embodiments, the supports can include bendable fiberglass tent poles. The supports 106 may be threaded through loops or holes (not shown) within the textile material to affix the textile material to the supports to support the tent structure. Supports can be configured into an arch as shown. Additionally, the supports can be configured in a crossing arrangement, or other suitable arrangement to provide support for the tent. The tent includes a front opening 102 and a rear opening 104. In embodiments, the front opening 102 and rear opening 104 are substantially identical. Thus, with the tent being opened at the front side and the back side, the tent effectively forms a tunnel portion comprised of a textile material with a front opening 102 at a front side of the tunnel portion and a rear opening 104 at a rear side of the tunnel portion. Embodiments may include a front panel 110 to provide additional support for the tent structure. In some embodiments, flaps may be used to seal the front opening 102 and/or rear opening 104 may have a flap or covering to seal the entrance to prevent ingress of snow during a snowfall.

Tent 100 further includes enclosure 116 which may be used to house various electrical, electronic, and/or mechanical components for the tent 100. The enclosure 116 may be affixed to the textile material 108 via a hook-and-loop fastener, or other suitable mechanism. In some embodiments, an opening may be formed within the tent fabric such that the enclosure extends from the outside of the tent to the inside of the tent. A power cord 112 extends from the enclosure 116, and includes plug 114 for use in a standard wall outlet. Other embodiments may utilize a different type of plug for connecting to other outlet types (e.g. a 220V outlet). In yet other embodiments, the power cord 112 may be connected to another power source such as a gas/diesel generator, battery, or other suitable power source. The tent 100 of disclosed embodiments includes a heating system for heating the textile material 108. In a usage scenario, the tent is assembled prior to a snowfall, such that it covers a portion of a driveway, yard, street, or other location for which it is desired to prevent snow accumulation. The heating system heats the textile material 108 such that falling snow that contacts the textile material 108 melts, thereby preventing snow accumulation on the ground surface covered by tent 100. In embodiments, the tent 100 may optionally be secured to the ground with additional ties, indicated generally as 109, which may be staked into the ground, secured to heavy objects such as bricks, cinderblocks, or sandbags, or secured in another suitable manner.

Figure 1B:
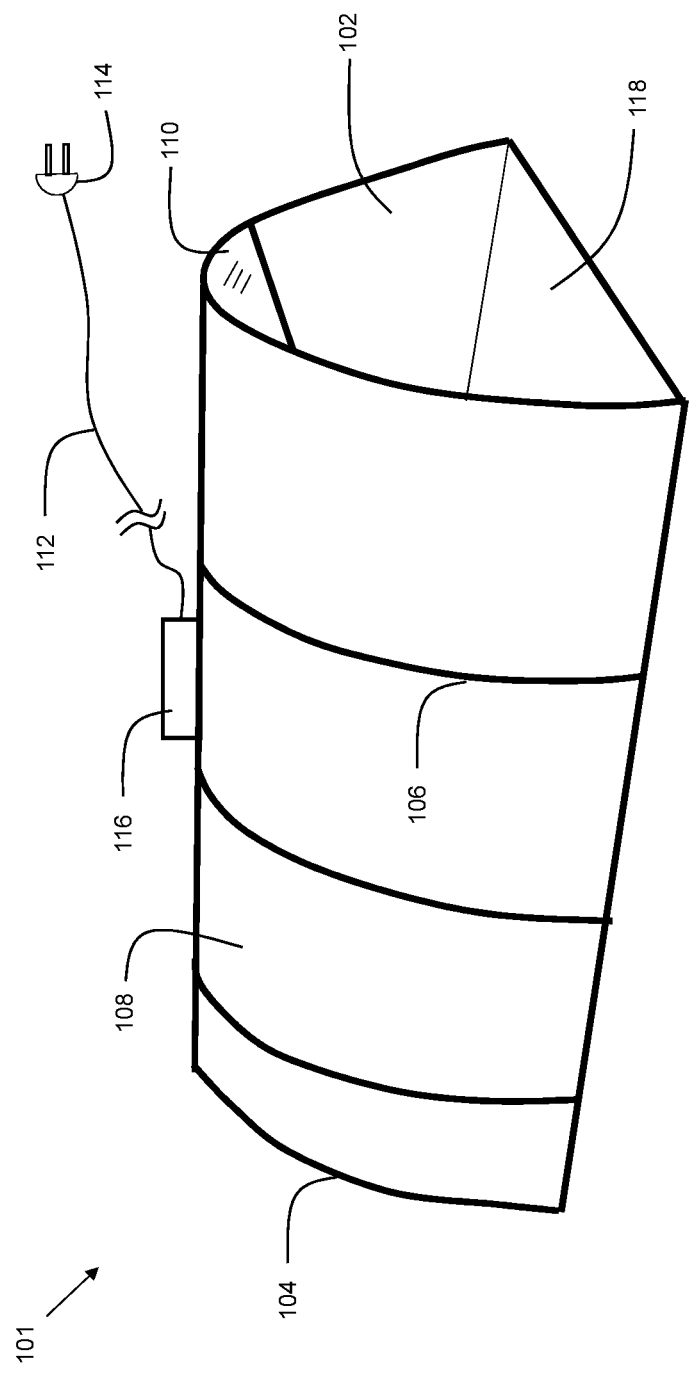
FIG. 1B shows a snow removal tent in accordance with another embodiment of the present invention.

FIG. 1B shows a snow removal tent 101 in accordance with another embodiment of the present invention. Snow removal tent 101 is mostly similar to tent 100 of FIG. 1B, with a key difference being the incorporation of a floor panel 118 into the tent. The floor panel may be used to further protect the underlying surface from snow. Additionally, objects, such as bricks, sandbags, and/or a vehicle, may be placed in the tent 101 and on top of, and in contact with, the floor panel 118. This provides additional weight to keep the tent stable and secured during use. In some embodiments, the heating system also applies heat to the floor panel 118. In other embodiments, only the textile material 108 is heated. The shape of the tent is preferably an arched tunnel, dome, or a slanted angled shape that promotes the ability of snow and/or water to slide off of the tent.

Figure 2:
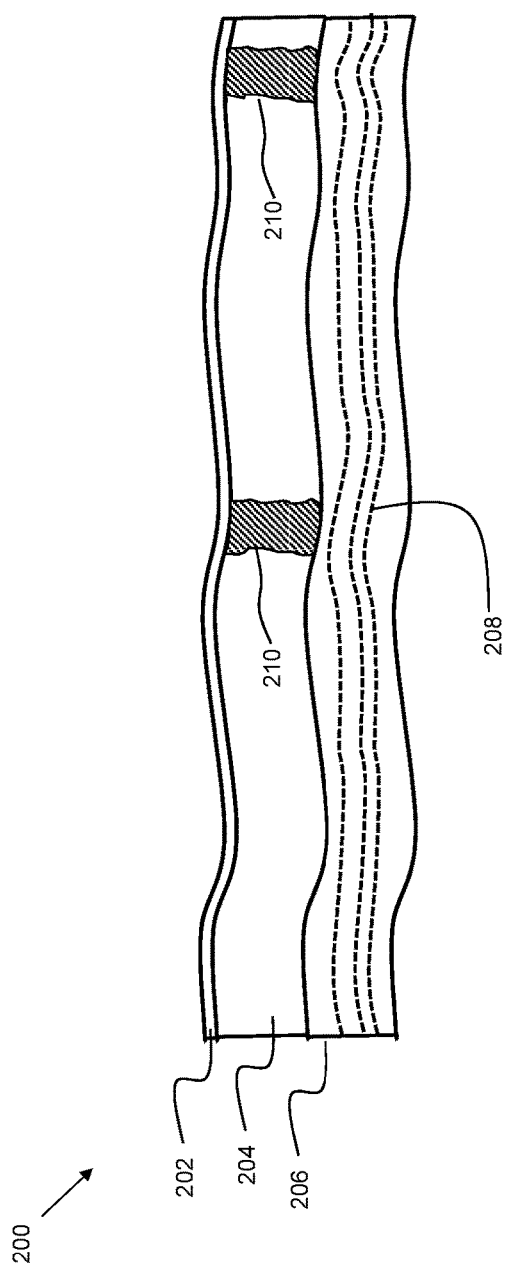
FIG. 2 shows a detailed cutaway view of a portion of textile material for a snow removal tent in accordance with another embodiment of the present invention.

FIG. 2 shows a detailed cutaway view of a portion of textile material 200 for a snow removal tent in accordance with another embodiment of the present invention. The textile material 200 is similar to material 108 shown in FIG. 1A and FIG. 1B. The textile material includes an outer layer 204. In embodiments, the outer layer 204 may be comprised of nylon and/or polyester. In some embodiments, optionally, a hydrophobic coating 202 is applied to the outer surface of outer layer 204. In embodiments, the hydrophobic coating 202 may include a wax, a fluoropolymer based coating, carbon nanotube coating, or other suitable hydrophobic treatment.

In embodiments, outer layer 204 is a ripstop layer, comprising reinforcing junctions 210 at periodic intervals. In embodiments, during the weaving/fabrication of the outer layer 204, the reinforcement junctions 210 are formed by utilizing reinforcement threads that are interwoven at regular intervals in a crosshatch pattern. The intervals are typically 5 to 8 millimeters. The reinforcement threads may be thicker than the other threads used in weaving/fabricating of the outer layer 204. Thus, in embodiments, the outer layer comprises a ripstop textile.

A heating layer 206 is disposed below the outer layer 204. Thus, in an assembled tent in accordance with embodiments of the present invention, layer 202 or layer 204 is exposed on the outside of the tent structure, while layer 206 is disposed on the interior of the tent structure. Layer 206 includes a plurality of heating elements, indicated generally as 208. In embodiments, heating elements 208 are comprised of insulated metal wires and/or carbon fiber wires. Thus, in some embodiments, the heating layer comprises a fabric layer comprising a plurality of insulated wire heating elements disposed within the fabric layer. In some embodiments, the heating layer comprises a fabric layer comprising a plurality of carbon heating elements disposed within the fabric layer.

During operation, electricity passes through the heating elements 208, which generate heat within the heating layer 206. The generated heat warms the outer layer 204 such that snow melts upon contact with the outer layer, transforming into liquid water. The water then slides down the outer surface of the tent to the ground, preventing accumulation of snow on the tent and the ground surface covered by the tent. In this way, an outdoor area such as a driveway, sidewalk, or other outdoor surface is protected from falling snow. When the snowfall is over, the tent can be removed, enabling usage of the outdoor area.

Figure 3:
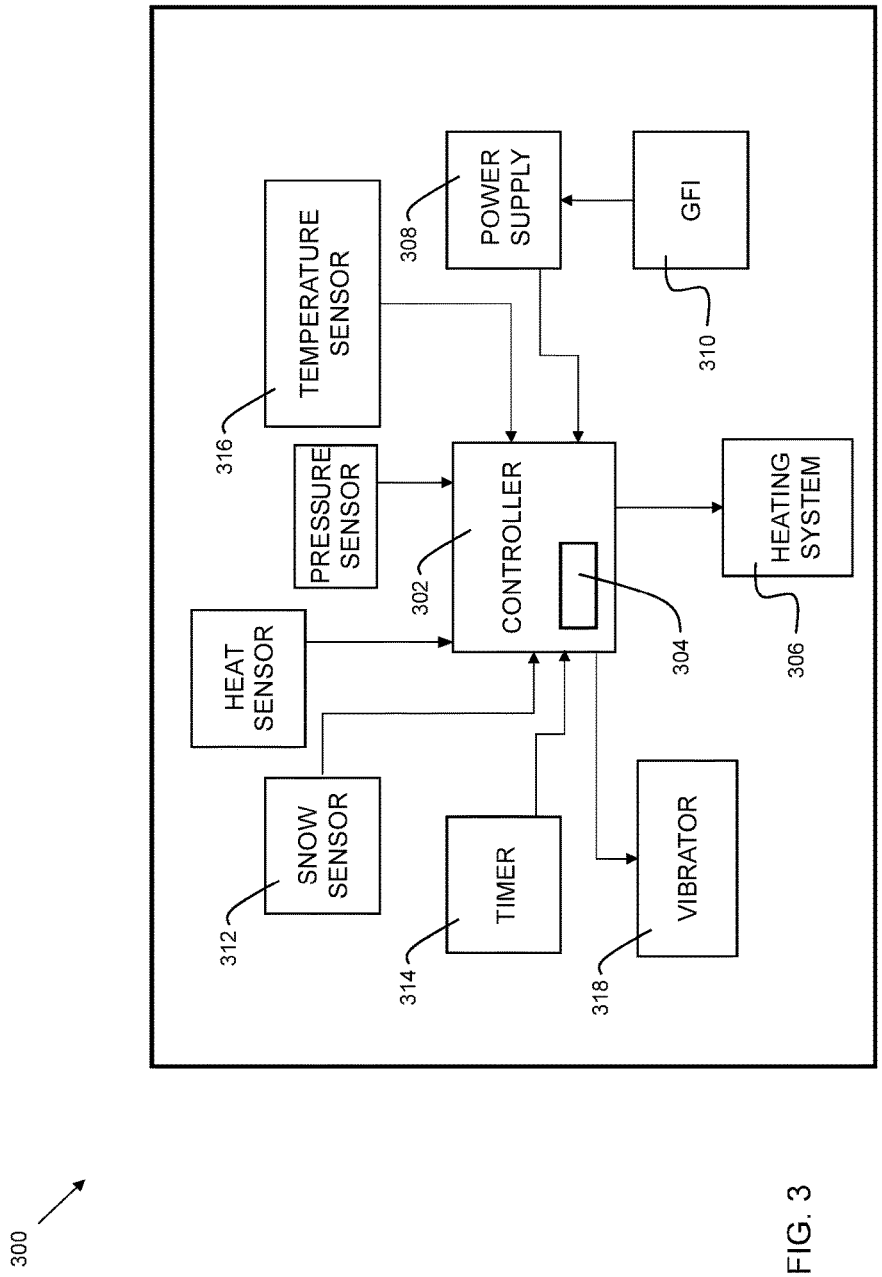
FIG. 3 shows a block diagram of components for a snow removal tent in accordance with another embodiment of the present invention.

FIG. 3 shows a block diagram 300 indicating various components for a snow removal tent in accordance with another embodiment of the present invention. In embodiments, some or all of the components shown in block diagram 300 may be contained within the enclosure (see 116 of FIG. 1A). Embodiments may include a controller 302. Controller 302 may be a microcontroller, microprocessor, or other suitable processor for executing instructions, processing input and output (I/O), and operating the heating system and/or other peripherals. The controller 302 may include onboard memory 304. The memory 304 may be a non-transitory computer readable medium including, but not limited to, flash, static random access memory (SRAM), and/or read-only memory (ROM). In other embodiments, the memory 304 may be external to the controller 302 and accessed by the controller via a memory bus or other suitable interface. The controller 302 comprises multiple input pins configured to receive electrical signals. Similarly, the controller 302 comprises multiple output pins configured to generate electrical signals.

In embodiments, the controller 302 is coupled to the heating system 306. In embodiments, the controller 302 is configured and disposed to activate the heating system 306 by asserting an output signal. The output signal may be configured to activate a relay, switch, or other suitable mechanism to activate the heating system, thus applying heat to the textile fabric of the tent. Similarly, the controller 302 can deactivate the heating system by deasserting the output signal.

Embodiments may include a snow sensor 312 coupled to the controller. The snow sensor 312 generates a signal output upon detecting the presence of snow. In response to detecting the asserted signal from the snow sensor 312, the controller 302 activates the heating system. In embodiments, the snow sensor may include, but is not limited to, an opto-electronic sensor, infrared proximity sensor, hot wire probe, ultrasonic sensor, mechanical probe, and/or weight sensor. In one embodiment utilizing the hot wire probe, the wire is heated to an elevated temperature (e.g. 100 degrees Celsius). When snow contacts the wire, it cools the wire which changes its resistance. The wire is part of a balanced bridge circuit that increases a voltage in response to the change in resistance. The voltage increase is interpreted as an asserted signal by the controller to activate the heating system. Other snow sensing techniques may be employed in embodiments of the present invention.

Embodiments may further include a temperature sensor 316. In embodiments, the temperature sensor 316 may be implemented utilizing a thermocouple, thermistor, and/or other temperature sensing components. In embodiments, the temperature sensor may be affixed to a portion of the textile material. In embodiments, multiple temperature sensors may be placed at various locations on the textile material of the tent. The temperature sensors are configured to assert an overtemp signal when the textile material exceeds a predetermined temperature (e.g. 110 degrees Celsius). When the predetermined temperature is exceeded, the overtemp signal is asserted, and the controller 302 then deactivates the heating system 306 as a safety measure, in the event of a short circuit or other malfunction.

Embodiments may further include a timer 314. In some embodiments, the timer may be implemented as a software process executed by the controller 302. In other embodiments, the timer 314 may be an external hardware timer. In embodiments, when the controller 302 activates the heating system 306, it also activates timer 314. Timer 314 expires after a predetermined time period (e.g. 10 hours). When the timer 314 expires, the controller 302 receives a timer signal, and in response to the timer signal, deactivates the heating system 306. In this way, the heating system automatically deactivates after the time period established by the timer 314, saving power by preventing the heating system from being activated indefinitely.

Embodiments include a power supply 308. The power supply 308 may include AC/DC conversion with multiple DC outputs for powering the controller 302 and associated peripherals, as well as a high current output for powering the heating system 306. One or more fuses may be integrated into the power supply for safety. In addition, a Ground Fault Interrupt (GFI) 310 may be integrated into the power supply, power cord (112 of FIG. 1A), or plug (114 of FIG. 1A). The GFI quickly shuts down the power in the event of sensing a loss of current, providing an additional safety mechanism for the tent.

Embodiments may optionally include a vibrator 318. The vibrator 318 may be an electromechanical device installed within the enclosure (e.g. 116 of FIG. 1A). The vibrator 318 is configured and disposed to impart vibrations to the tent to promote snow sliding/falling off the tent textile material surfaces. In embodiments, the vibrator 318 is activated and deactivated at the same time as the heating system 306. In embodiments, the vibrator 318 is configured to impart vibrations to the tent at a frequency ranging from 30 hertz to 120 hertz. Other frequencies are possible in some embodiments. Thus, some embodiments can include a vibrator mechanism disposed within the enclosure.

Figure 4:
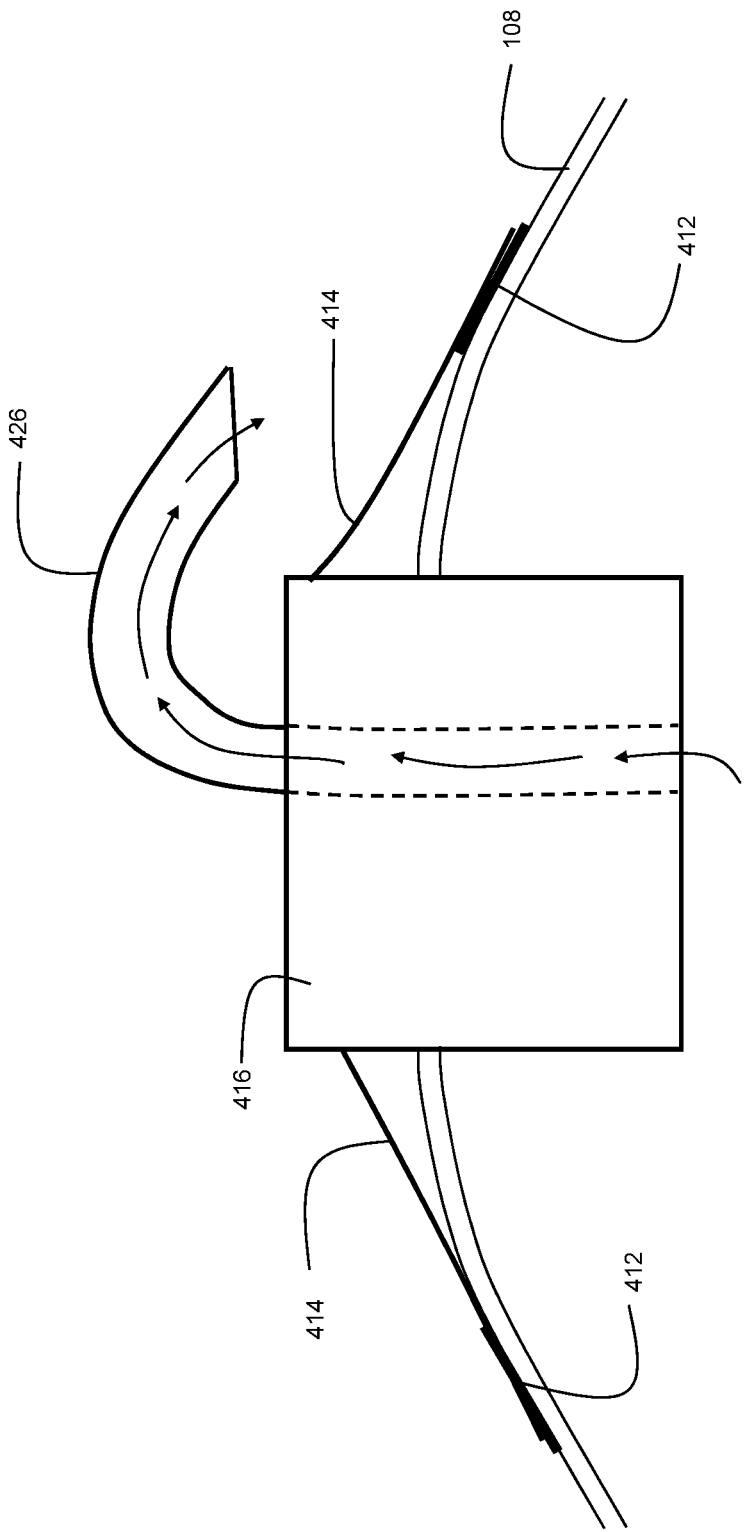
FIG. 4 shows a detailed cutaway view of a portion of a vent for a snow removal tent in accordance with another embodiment of the present invention.

FIG. 4 shows a detailed cutaway view of a portion of a vent for a snow removal tent in accordance with another embodiment of the present invention. In such an embodiment, there is a cutaway formed within the textile material 108. Enclosure 416 is configured and disposed to traverse the cutaway such that a portion of the enclosure 416 is above, and outside of the tent, and another portion of the enclosure 416 is below, and inside of the tent. A vent 426 is formed in the enclosure 416. In embodiments, the vent 426 comprises an Inverted-U conduit extending from the enclosure to a point above the top of the tunnel portion. Since snowfall often occurs during windy conditions, it can be desirable to provide a vent within the tent to allow some air to pass from within the tent to the outside of the tent through the vent. This relieves pressure on the tent to reduce the risk of the tent being damaged or becoming unsecured during windy conditions. In embodiments, a plurality of straps, indicated generally as 414 may be used to secure the enclosure 416 to the tent via hook-and-loop fastener pads 412. Other mechanisms for securing the enclosure 416 to the tent may also be used in some embodiments. Thus, in embodiments, an enclosure is affixed to a top portion of the tunnel portion. In addition to housing the vent 426, enclosure 416 may also house one or more of the components shown in FIG. 3.

Figure 5A:
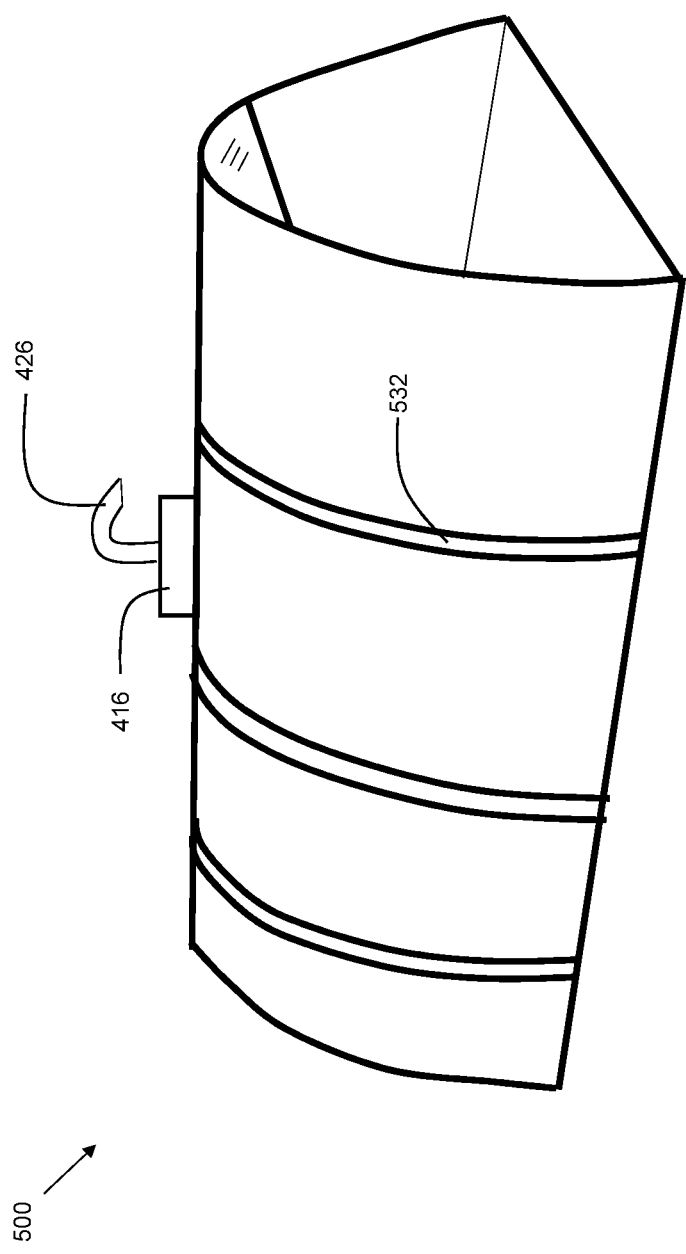
FIG. 5A shows a snow removal tent in accordance with another embodiment of the present invention that utilizes a conduit vent.

FIG. 5A shows a snow removal tent 500 in accordance with another embodiment of the present invention that utilizes a vent 426. The tent 500 includes a textile material and heating system similar to the previously described embodiments. Tent 500 illustrates air support tubes 532 that are used in place of support poles. In embodiments, the air support tubes 532 are inflated to a pressure where the air support tubes 532 form an arch shape to provide structure for the tent. Thus, embodiments include a plurality of air support tubes disposed around the tunnel portion of the tent. Note that while air support tubes 532 are shown in the embodiment of FIG. 5, air support tubes 532 may also be used instead of, or in addition to, the supports 106 utilized in the embodiments of FIG. 1A and FIG. 1B. This embodiment also includes the heating system as previously described and may also include one or more additional components such as those illustrated in FIG. 3.

Figure 5B:
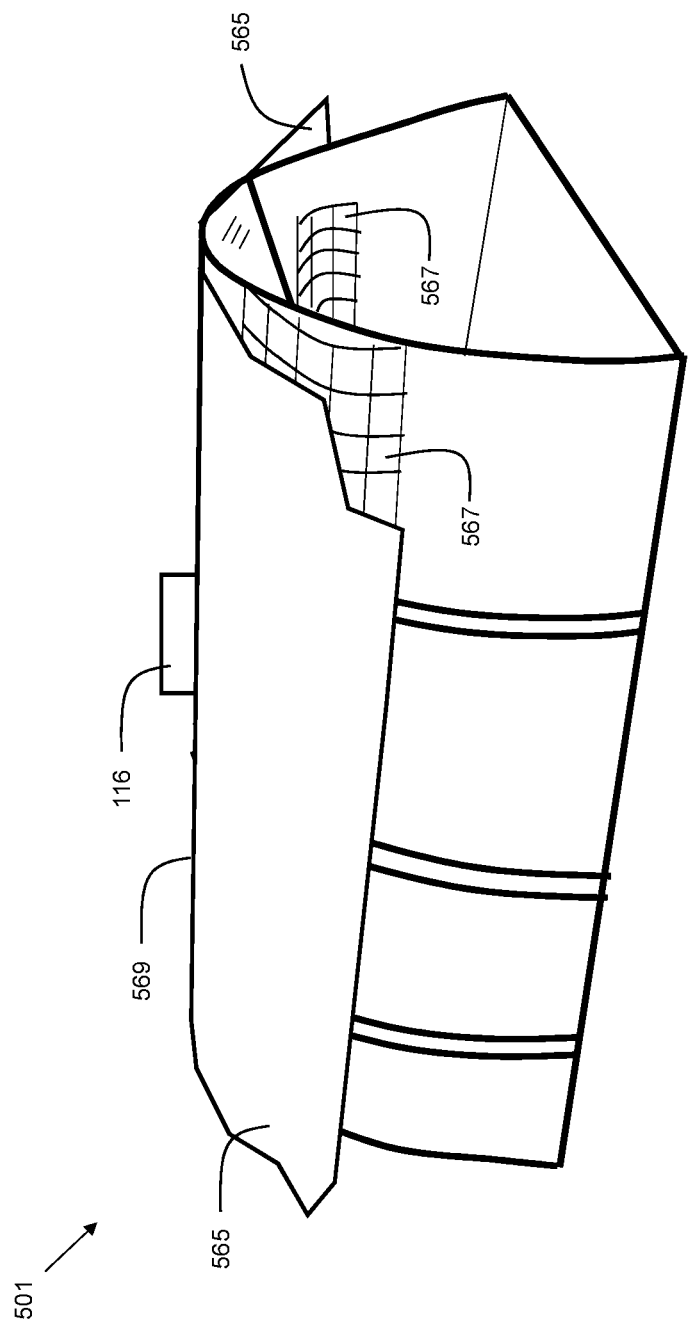
FIG. 5B shows a snow removal tent in accordance with another embodiment of the present invention that utilizes a mesh vent.

FIG. 5B shows a snow removal tent 501 in accordance with another embodiment of the present invention that utilizes a mesh vent. Tent 501 includes a mesh area 567 on each side of the tent 501. The mesh area may be comprised of nylon, metal, or other suitable material that has openings allowing air to pass therethrough. Snow flaps 565 are affixed to the top 569 of the tent 501 but are unattached on the sides of the tent. In this way, a wind gust that enters the tent can pass though the tent by way of the mesh vent. The snow flaps 565 may move a distance away from the tent to allow the wind gust to pass through. In this way, the snow removal tent 501 is more resistant to strong winds. In some embodiments, the snow flaps 565 may be comprised of a material such as depicted in FIG. 2, with heating elements to prevent accumulation of snow on the snow flaps 565. Thus, embodiments include a tent having a mesh vent with heated snow flaps flexibly attached to the tent at a top surface of the tent.

Figure 6A:
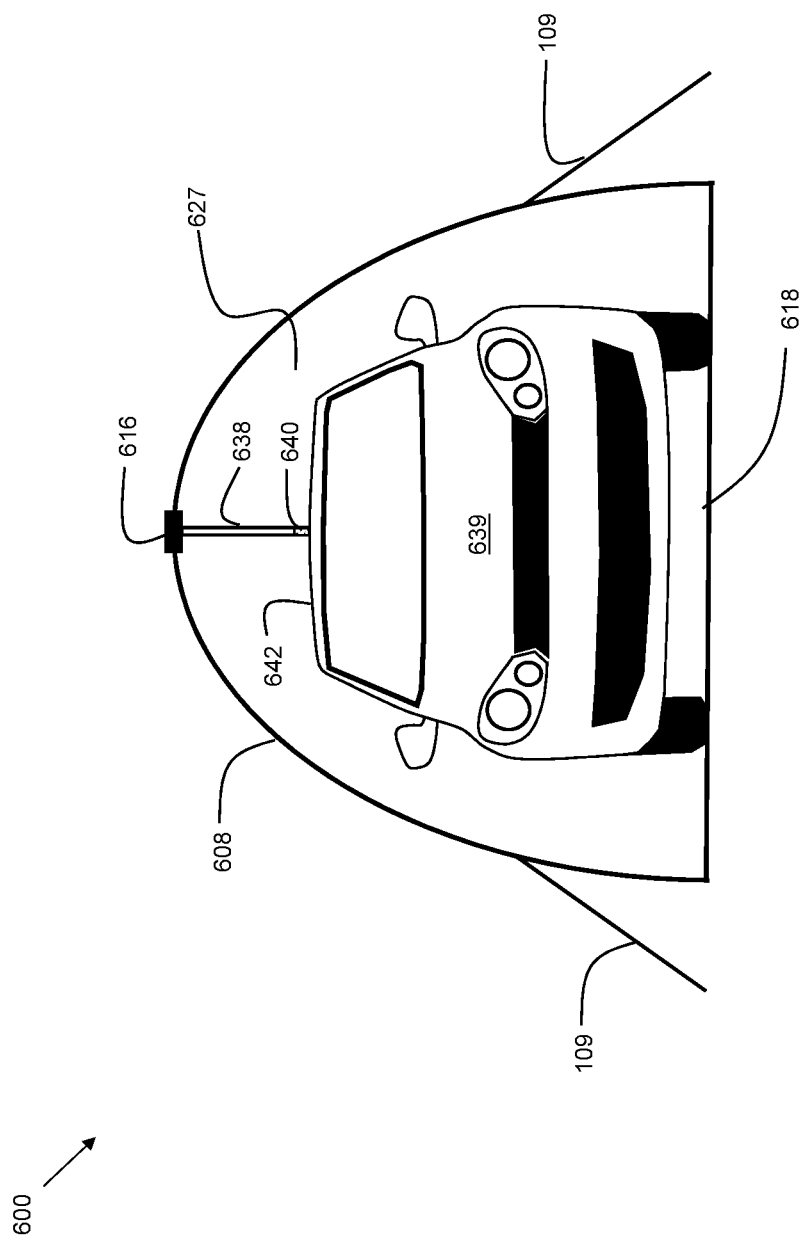
FIG. 6A shows a snow removal tent in accordance with another 5 embodiment of the present invention that utilizes a vehicle support strut.

FIG. 6A shows a snow removal tent 600 in accordance with another embodiment of the present invention that utilizes a vehicle support strut. In this embodiment, a vehicle 639 is parked within the tunnel portion 627 of the tent 600 during use. The vehicle 639 is in direct physical contact with floor panel 618. This provides a significant anchor for the tent 600 to prevent it from moving during windy conditions. The tent 600 may further include ties 109 that may be secured to the ground via stakes or other suitable mechanism to provide further support.

Tent 600 further includes vehicle support strut 638. Vehicle support strut 638 extends from a roof-mounted enclosure 616 (mounted to the roof of the tent, as shown in FIG. 4), and the distal end of the strut 638 includes a magnetic mount 640 that secures to the metal roof 642 of vehicle 639. In embodiments, the strut 638 may be a telescoping strut that can be adjusted to accommodate the different height of various vehicle types. The vehicle support strut 638 serves to provide additional structural support, taking advantage of vehicle 639 parked within tent 600. In this way, the tent 600 holds its arch shape, promoting the falling/sliding of snow and melted snow off of the textile material 608. This embodiment protects the driveway (or other area) where the tent 600 is set up, and also prevents snow and ice from forming on vehicle 639, thus providing even greater convenience for a user. This embodiment also includes the heating system as previously described and may also include one or more additional components such as those illustrated in FIG. 3. In some embodiments, the snow removal tent may simply be placed over a vehicle as a tarp, with no support poles in use.

Figure 6B:
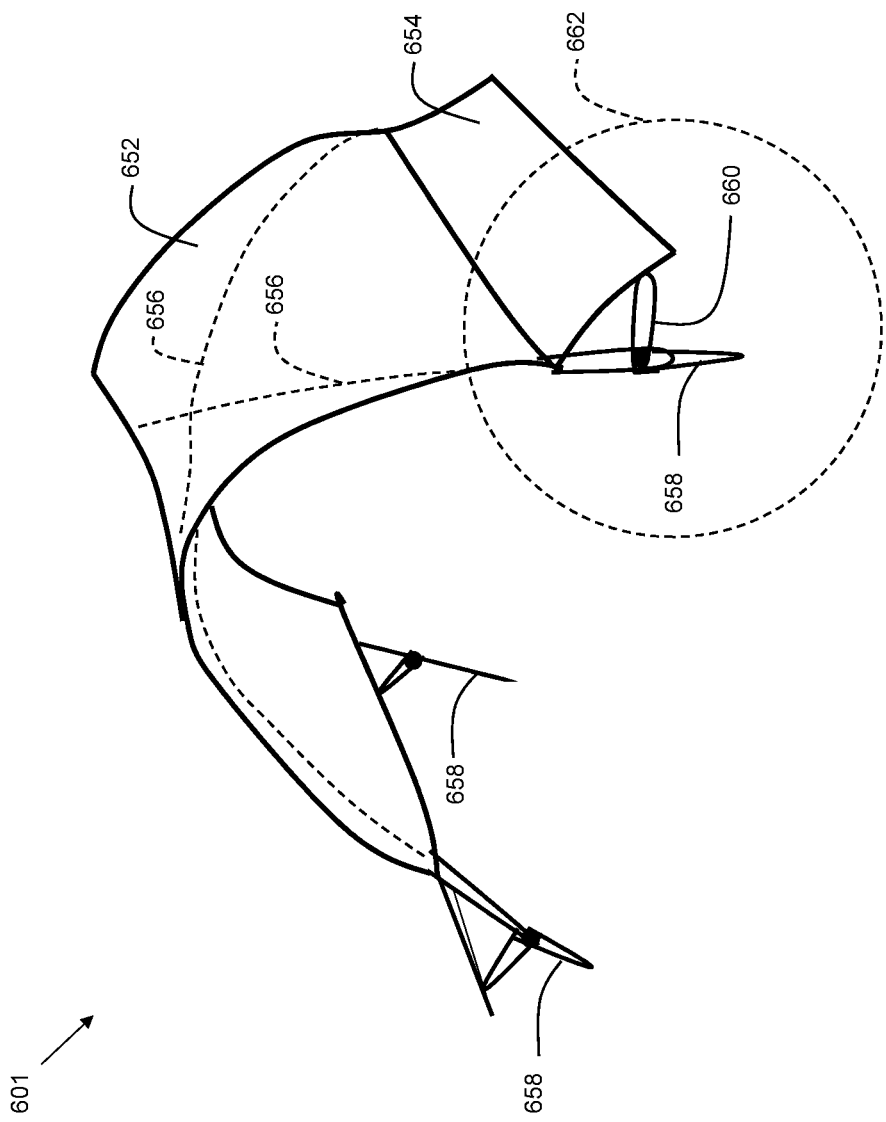
FIG. 6B shows a snow removal tent in accordance with yet another embodiment of the present invention.

FIG. 6B shows a snow removal tent 601 in accordance with another embodiment of the present invention. This embodiment includes a main tent covering 652 supported by two flexible poles indicated generally as 656. In embodiments, the poles may be configured in a crossing arrangement as depicted in FIG. 6B. Tent 601 further includes skirt panel 654. Skirt panel 654 covers the stakes, indicated generally as 658. This prevents snow from covering the stakes, thereby simplifying removal of the tent after a snowfall. Embodiments may include an extension strut 660 that is rotatably attached to the stake 658.

Figure 6C:
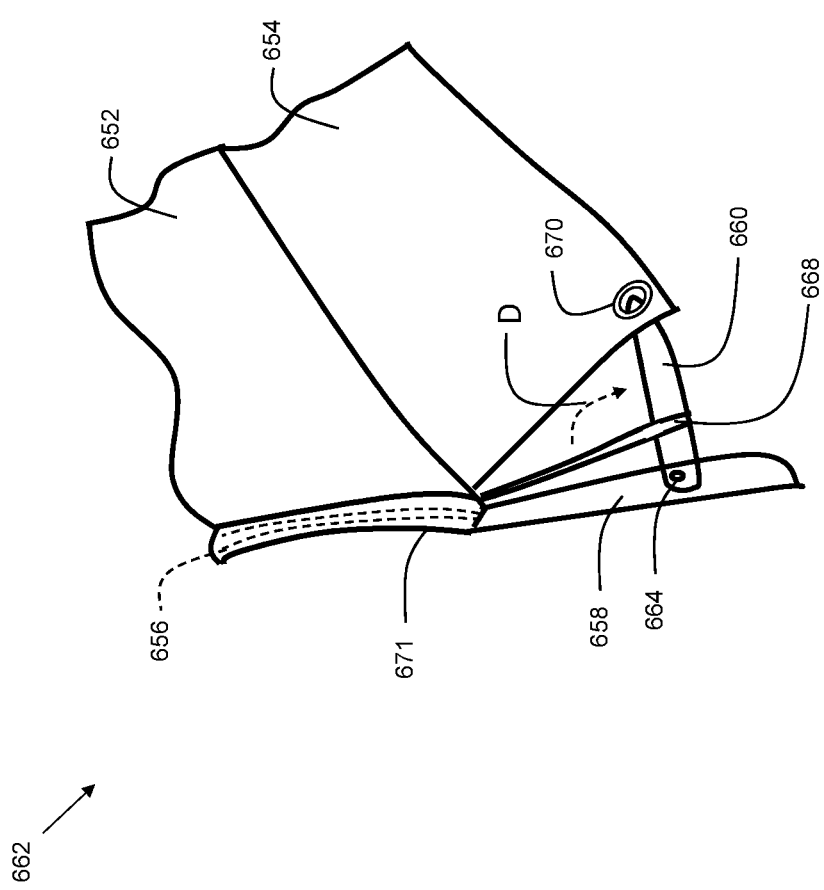
FIG. 6C shows additional details of the snow removal tent of FIG. 6B.

FIG. 6C shows additional details of the extension strut 660 and details of the area depicted as 662 in FIG. 6B. Referring now to FIG. 6C, the extension strut 660 is rotatably attached to stake 658 with rotation joint 664. In embodiments, the stake 658 is affixed to the pole 656. The pole 656 may be placed into a sleeve 671 at the edge of the main tent covering 652, thereby providing support for the tent. During assembly, the extension strut 660 is rotated in the direction indicated by arrow D. In embodiments, the distal end of the extension strut 660 is placed through a grommeted ring 670 formed in the skirt panel 654. In some embodiments, an adjustable strap 668 is affixed to the main tent covering 652, and attaches to the extension strut 660 to provide additional tension for the main tent covering 652. This further increases the tautness of the main tent covering 652. As stated previously, the skirt panel 654 provides the advantage of protecting the stakes from snowfall, allowing for easier removal of the tent once the snowfall is complete. The skirt panel 654 may be used with the various embodiments within this disclosure.

Figure 7:
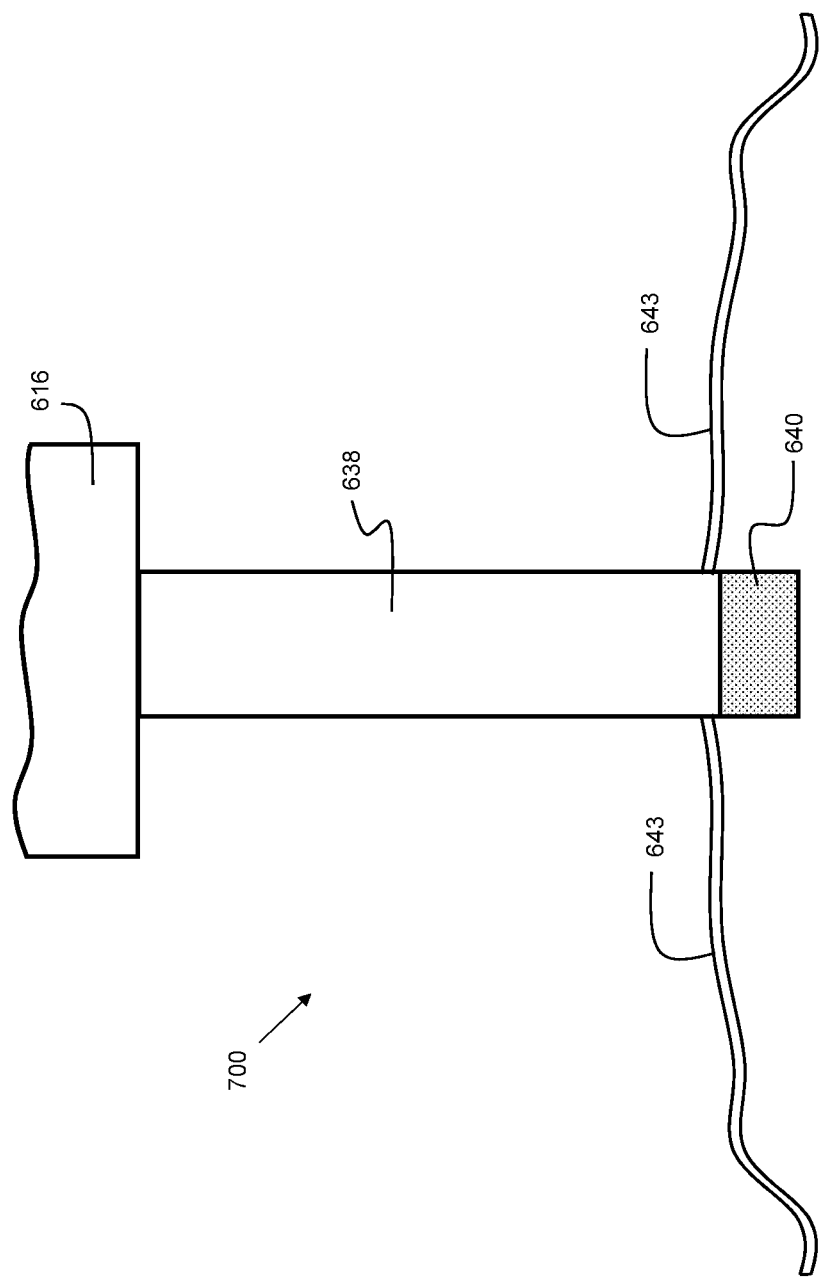
FIG. 7 shows a detailed view of a vehicle support device for a snow removal tent in accordance with another embodiment of the present invention.

FIG. 7 shows a detailed view of a vehicle support device 700 for a snow removal tent in accordance with another embodiment of the present invention. Support device 700 includes strut 638 that is affixed to roof-mounted enclosure 616. The strut 638 includes a magnetic mount 640 on the distal end. In embodiments, the magnetic mount 640 may include a neodymium magnet. During use, the magnetic mount 640 may be attached to the metal roof of a vehicle. Additionally, device 700 includes a plurality of mounting straps 643. The mounting straps 643 can be secured to a vehicle within the tent to provide additional stability for the tent. Thus, in embodiments, the support device includes a strut extending downward from the enclosure, where the strut further includes a plurality of flexible straps mounted on or near a distal end of the strut.

Figure 8:
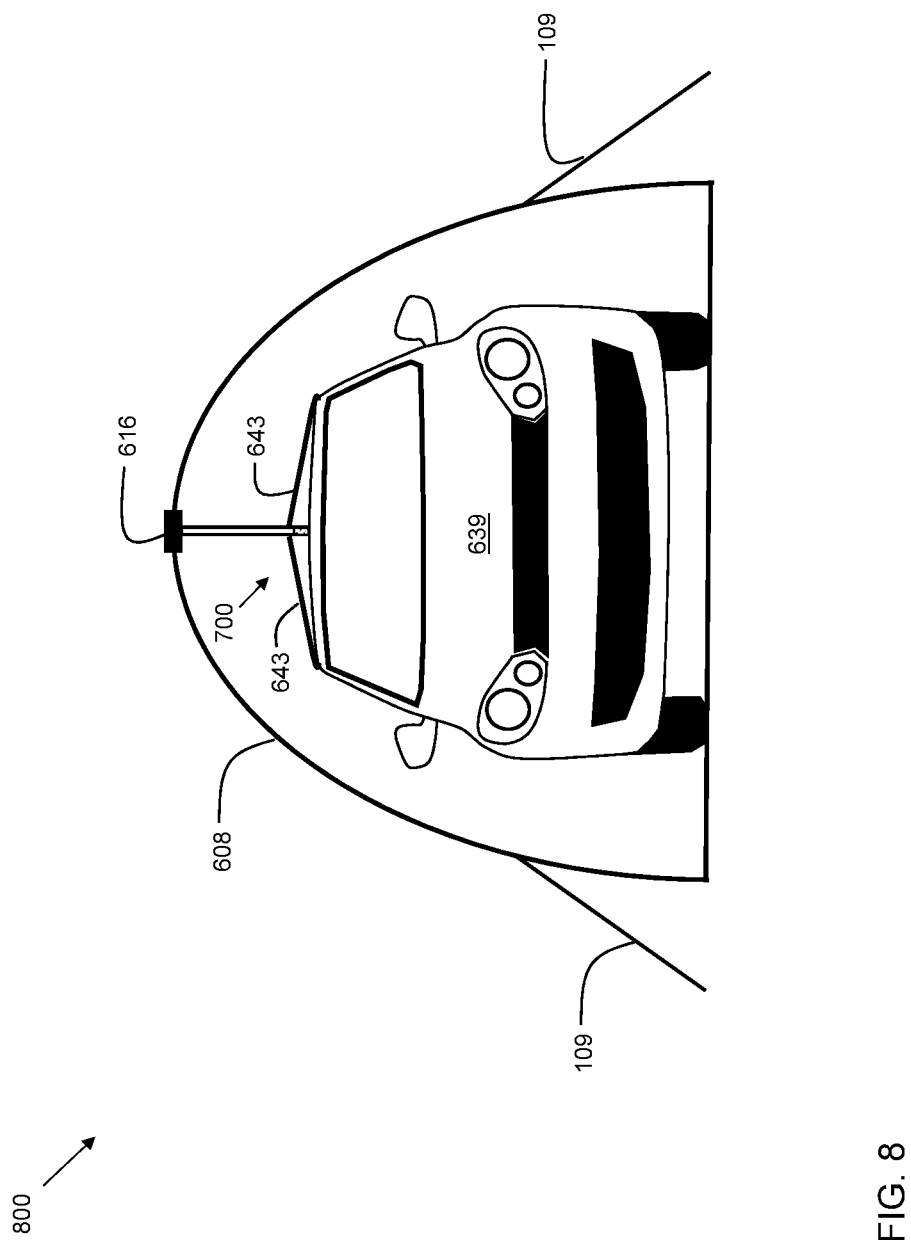
FIG. 8 shows a snow removal tent in accordance with another embodiment of the present invention that utilizes the vehicle support strut of FIG. 7.

FIG. 8 shows a snow removal tent 800 in accordance with another embodiment of the present invention that utilizes the vehicle support device of FIG. 7. Tent 800 is similar to tent 600, with the key difference being the use of vehicle support device 700. The straps 643 can be pulled through door openings in the vehicle 639. The vehicle door is then closed, securing the straps to the vehicle. This provides additional stability during windy conditions. This embodiment also includes the heating system as previously described and may also include one or more additional components such as those illustrated in FIG. 3.

Figure 9:
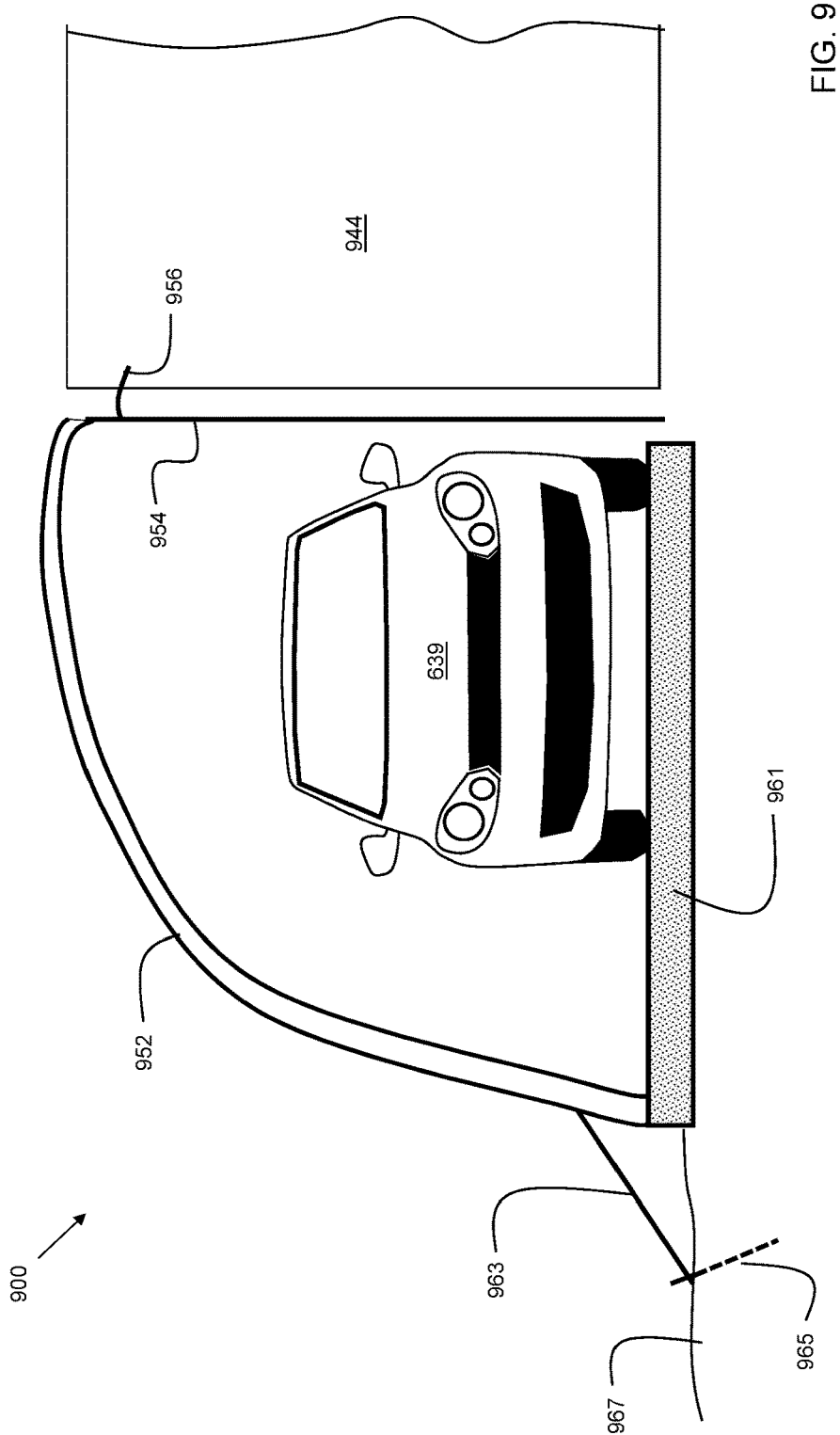
FIG. 9 shows a partial enclosure snow removal tent in accordance with another embodiment of the present invention.

FIG. 9 shows a partial enclosure snow removal tent 900 in accordance with another embodiment of the present invention. This embodiment is well-suited to a use case involving a driveway located adjacent to a building structure. Referring to FIG. 9, snow removal tent 900 is configured to be installed with support pole 954. While one support pole is shown in this view, in practice, there can be multiple poles installed at various intervals along the length of the tent. In embodiments, support pole 954 is secured to building 944 via strap 956. The strap may include a tie down, window mount, door mount, or other suitable mount to secure to the building. A plurality of flexible supports and/or air tube supports may be used to create the curved shape of the textile material 952. This embodiment also includes the heating system as previously described and may also include one or more additional components such as those illustrated in FIG. 3.

During use, tents of disclosed embodiments may be erected over a driveway or other surface for which it is desirable to keep the surface clear of snow. As shown in FIG. 9, tent 900 is erected over a concrete slab driveway 961. In some embodiments, the tent 900 may optionally be secured to the ground with additional ties, indicated generally as 963. In embodiments, the ties may be secured to the ground via stakes, indicated generally as 965. Often, there is a lawn surface adjacent to a residential driveway. As shown, the stake 965 is inserted into the lawn area 967 to provided further stability for tent 900. Any of the other embodiments disclosed herein may also be installed over a driveway in a manner similar to that shown in FIG. 9.

Figure 10:
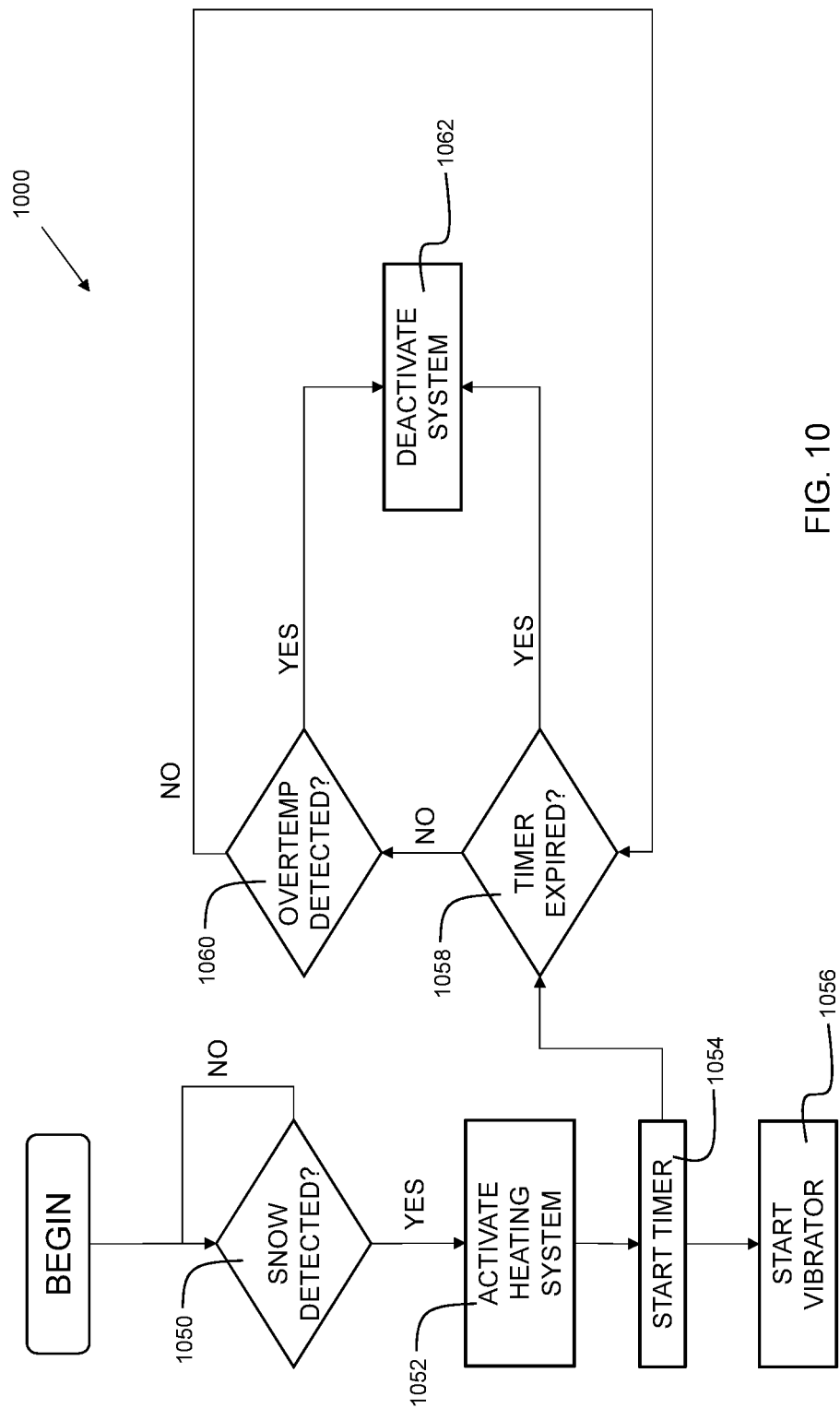
FIG. 10 shows a flowchart indicating process steps for embodiments of the present invention.

FIG. 10 shows a flowchart 1000 indicating process steps for embodiments of the present invention. In embodiments, the steps depicted in FIG. 10 may be implemented on a controller such as controller 302 shown in FIG. 3. In process step 1050, the presence of snow is detected. This can be performed via snow sensor 312 (FIG. 3). The presence of snow is periodically/continuously monitored. If snow is detected, the process continues to process step 1052 where the heating system is activated. In process step 1054 a timer is started. Optionally, in process step 1056, a vibrator is started. The vibrator imparts vibrations to the tent to encourage snow, sleet, slush, and/or water to slide down the tent surface to the ground. In process step 1058 a check is made to determine if the timer expired. If not, the process continues to checking if an overtemp condition is detected at process step 1060. If an overtemp condition is detected, or the timer expires, the system is deactivated in process step 1062. This includes deactivation of the heating system, and the vibrator for embodiments utilizing a vibrator. Note that in some embodiments, one or more steps may be performed in a different order, or may be performed concurrently.

Figure 11:
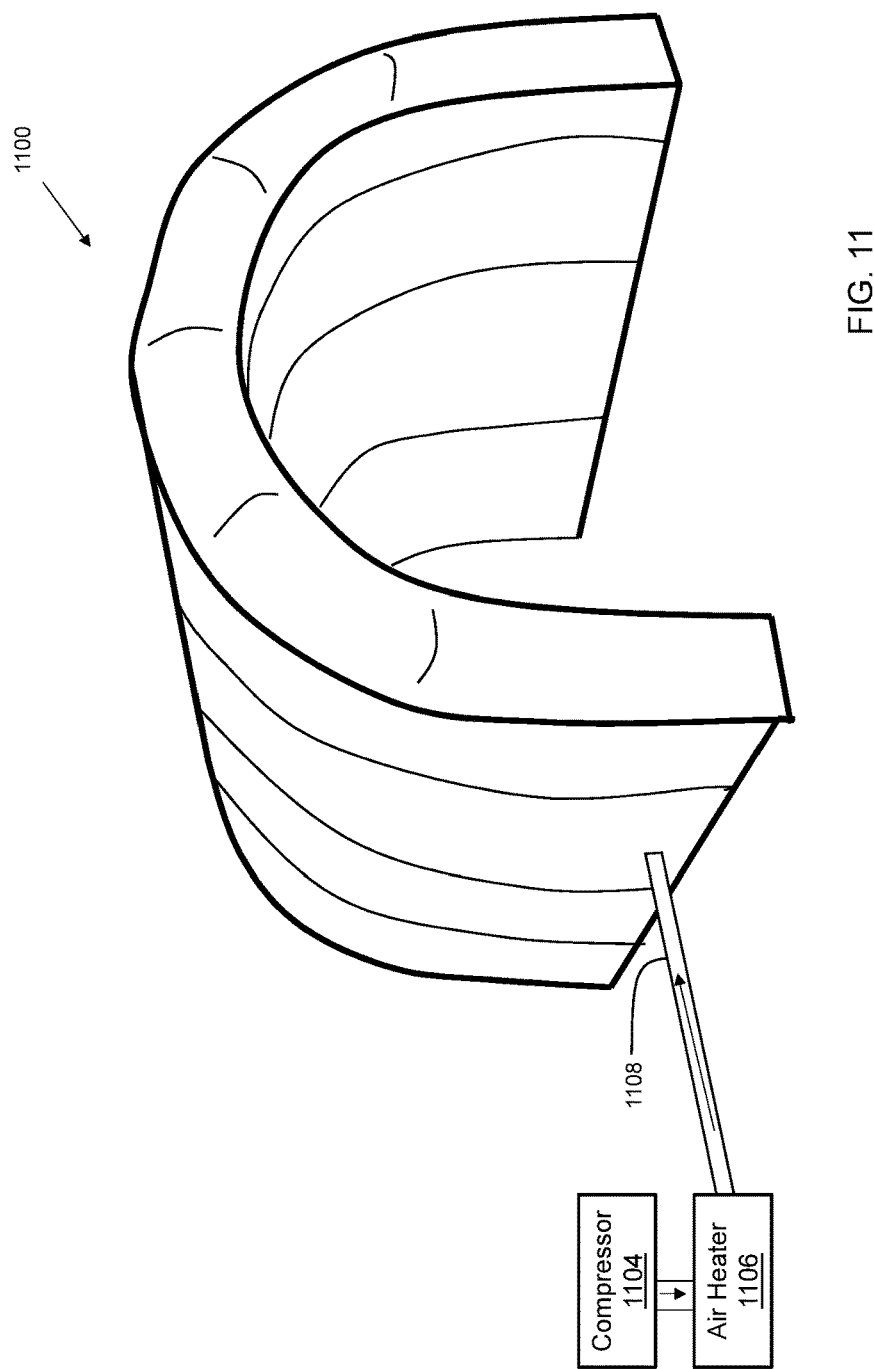
FIG. 11 shows another embodiment of the present invention.

FIG. 11 shows another embodiment of the present invention. Tent 1100 is an inflatable tent that utilizes a constant air pressure source of a compressor 1104. The compressor 1104 can be powered by an electric motor, an internal combustion engine, or other suitable power source. Air output from the compressor 1104 is fed to an air heater 1106. In embodiments, the air heater 1106 is an electric air heater. The air heater 1106 elevates the temperature of the air prior to the air flowing through conduit 1108 into the tent 1100. The tent 1100 is partially porous, allowing for a certain amount of leakage of air from tent 1100. Thus, air within tent 1100 is continuously replenished by warm air from conduit 1108. In embodiments, the air entering the conduit 1108 from air heater 1106 is at a temperature ranging from 35 degrees Celsius to 60 degrees Celsius. In this embodiment, the tent 1100 may be comprised of conventional materials without heating elements integrated into the materials. The tent 1100 may be treated with a hydrophobic coating (see 202 of FIG.

2). The heat from the heated air that fills the inflatable tent warms the tent surface, causing falling snow to melt on contact. Thus, embodiments can include a system comprising an inflatable tent, a compressor configured and disposed to output air into an air heater, where the air heater heats air prior to supplying the air to the inflatable tent.

In yet other embodiments, a conventional tent may be used with a heater operated within the tent. In embodiments, the heater can be an electric space heater, kerosene space heater, or other suitable space heater. The space heater provides heat to the surface of the tent, causing falling snow to melt on contact with the tent surface.

Figure 12:
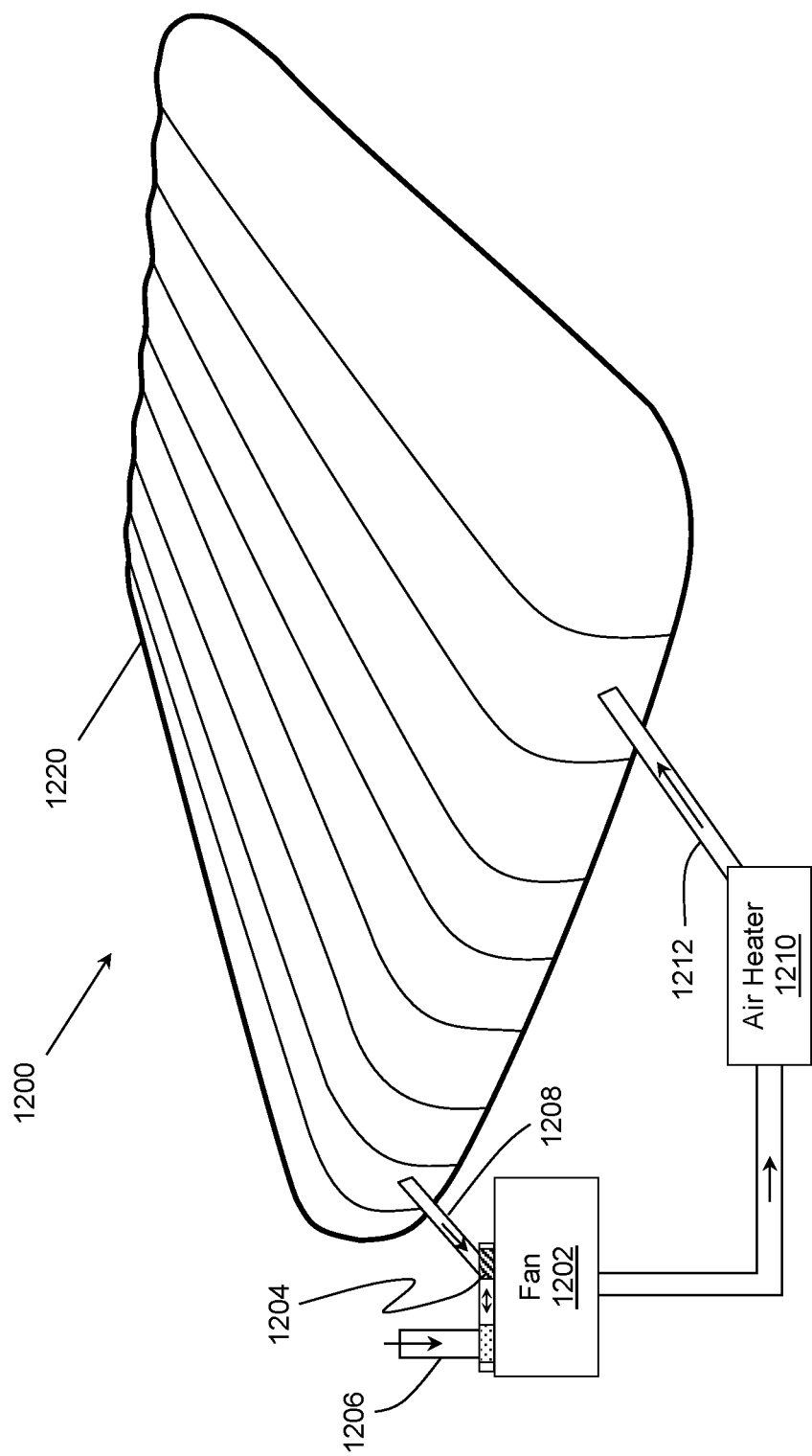
FIG. 12 shows a snow removal air mattress in accordance with embodiments of the present invention.

FIG. 12 shows another embodiment of the present invention. As shown, air mattress 1200 includes a substantially flat inflatable portion 1220 that can be rested on a flat surface, such as a driveway or sidewalk, although other shapes may be included. The inflatable portion 1220 may be or comprise a textile, which may include nylon or polyester for example, and may include a ripstop material. In the embodiment shown, fan 1202 inflates the inflatable portion 1220 with outside air drawn through air inlet 1206. Air divider 1204 directs air from the outside to fan 1202, which pushes the air past air heater 1210 and into the inflatable portion 1220 through conduit 1212. When inflatable portion 1220 is fully inflated, air divider 1204 is adjusted to close air inlet 1206 and open air circulating conduit 1208. Fan 1202 then draws air from inside the inflatable portion past heater 1210 and through conduit 1212 back into the inflatable portion. The heated air inside the inflatable portion is thereby constantly or intermittently reheated and recirculated through the mattress.

The elements described in the foregoing can be disposed outside of inflatable portion 1220 as shown in FIG. 12. Alternatively, one or more of the elements may be disposed inside of the inflatable portion 1220. For example, FIGS. 13A, 13B, and 13C illustrate an embodiment in which divider 1204, fan 1202, and heater 1210 are all located inside enclosure 1312, which is disposed within inflatable portion 1220.

Figure 13A:
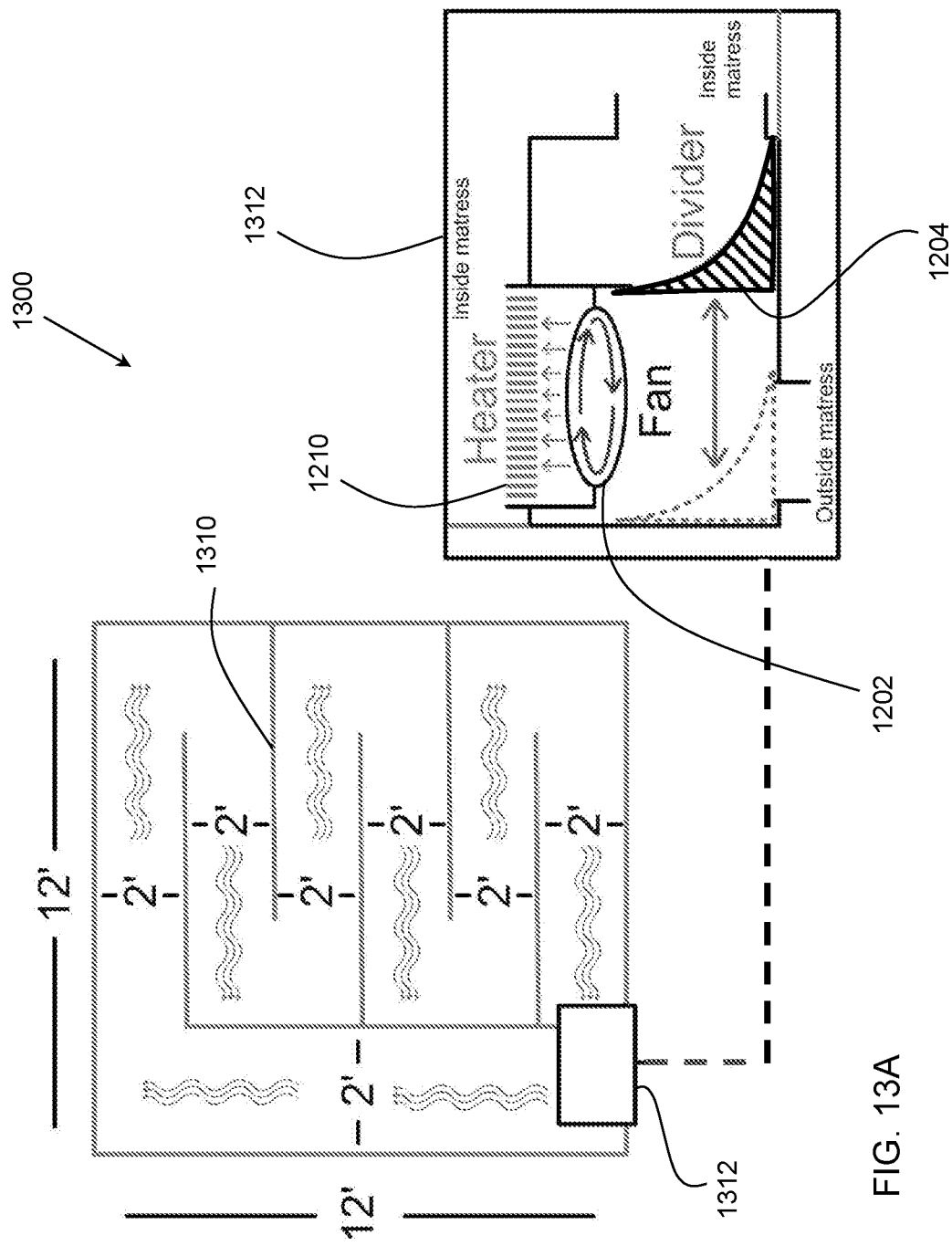
FIG. 13A shows a block diagram of components for a snow removal mattress in accordance with another embodiment of the present invention.

FIG. 13A shows another embodiment of an air mattress 1300 in which air is reheated and circulated in the inflatable portion. The outside dimensions of the air mattress are shown as 12'×12', although other dimensions may be used. Moreover, the dimensions do not need to form a square. For example, the 12×12 mattress may be sized to keep a particular driveway clear of snow. A narrower, longer driveway may benefit from a narrower, longer air mattress, such as 10'×20' for example (not shown). A sidewalk may be kept snow free with an even narrower and longer configuration, such as 5'×25' for example (not shown).

As shown in FIG. 13A, baffles 1310 are illustrated that are configured and disposed to direct air throughout the interior of the inflatable portion. Baffles 1310 may attach to both a top interior surface and a bottom interior surface of the air mattress to form one or more tunnels through the interior of the mattress. The baffles 1310 are shown to define pathways that are 2' wide, although other dimensions may be used. The baffles are shown to form pathways that are substantially either parallel or perpendicular to each other, although other configurations may be used. The baffles may be made of a flexible material such as a textile that does not provide structural support. Alternatively, some or all of the baffles may be made of stiffer material that provides structural support. Pathways through the inflatable portion may alternatively or in addition be defined using elements other than baffles. For example, tubes may be used to carry heated air from the heater to opposite sides of the inflatable portion, or to intermediate locations, or both (not shown).

Figure 13B:
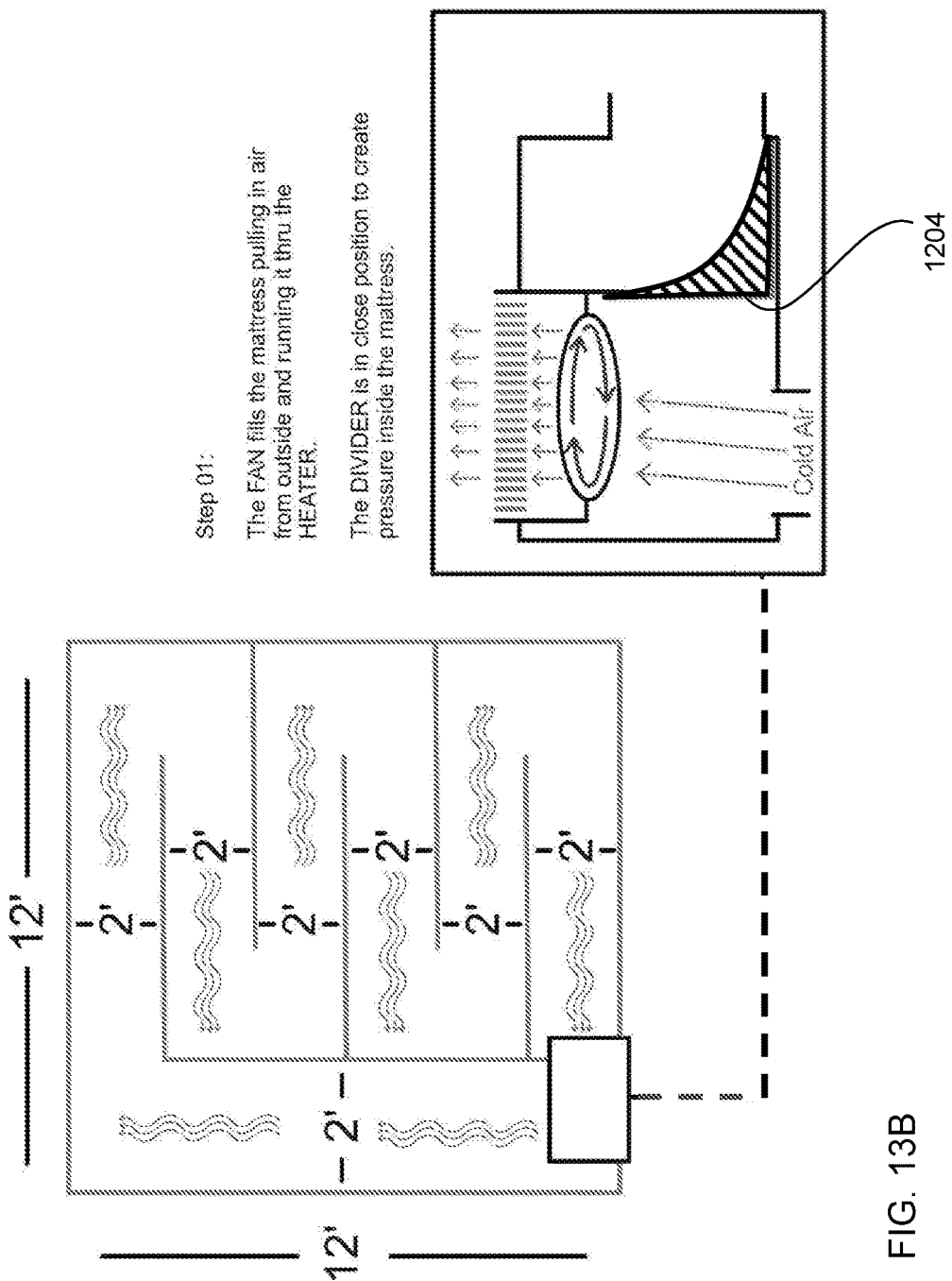
FIG. 13B shows the block diagram of FIG. 13A showing air from outside the mattress being heated and blown into the mattress.
Figure 13C:
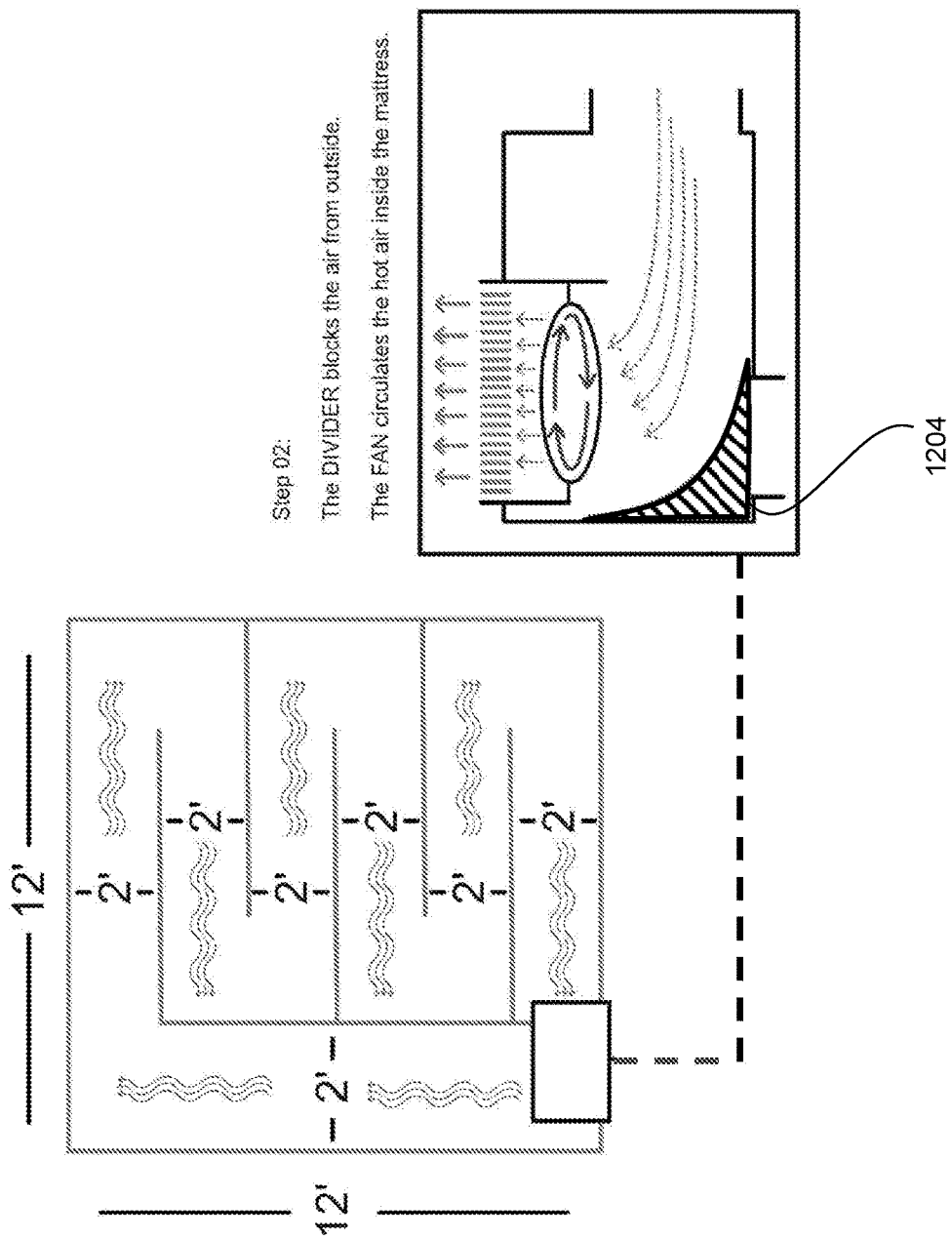
FIG. 13C shows the block diagram of FIG. 13A showing air from inside the mattress being heated and circulated through the mattress.

FIG. 13B shows the air divider 1204 in a position wherein fan 1202 draws outside air into the inflatable portion. Fan 1202 pushes the air past heater 1210 to inflate the mattress with heated air. After the mattress is inflated, divider 1204 may be reconfigured to block outside air, and instead circulate the air inside the inflated mattress, as shown in FIG. 13C.

The fan, heater, and divider illustrated in the foregoing figures may be controlled by a controller operatively coupled to each, similar to the controller illustrated in FIG. 3. In embodiments, the inflated portion is inflated, heated, and maintained by the controller based on input obtained from one or more sensors. For example, the air divider may initially be configured by default to permit the fan to draw outside air to inflate the inflatable portion, and the air heater may be configured by default to heat the air as it inflates the inflatable portion. The system may be activated based on a signal provided to the controller by a snow sensor that senses contact with snow or ice.

A pressure sensor may be disposed and configured to provide a signal to the controller when the pressure in the inflatable portion reaches a predetermined pressure threshold. When that threshold is reached, the controller may adjust the divider to block outside air, and to circulate the air in the inflated portion. When the pressure drops below the same or a different predetermined pressure threshold, the controller may adjust the divider to block circulating air and admit outside air to increase the pressure inside the inflated portion.

A heat sensor may be disposed and configured to provide a signal to the controller when the temperature of the air at a predetermined location inside the inflatable portion exceeds a predetermined temperature threshold. When that threshold is reached, the controller may reduce the heat output of the air heater, or turn it off altogether. Then the temperature drops below the same or a different predetermined temperature threshold, the controller may adjust the air heater to increase the temperature of the air inside the inflatable portion. Alternatively or in addition, the controller may adjust the fan speed or turn off the fan based on predetermined criteria.

As can now be appreciated, disclosed embodiments provide apparatus and methods for keeping an outdoor area clear of snow and other types of frozen precipitation. An inflatable mattress, tunnel, or other shape may be disposed over the area to be kept clear of snow. A snow sensor detects the presence of snow. Upon detecting the presence of snow, a fan and heating system are activated to inflate and heat the inflatable portion to melt falling snow upon contact. The air inside the inflatable portion is continually or intermittently reheated and circulated. The water from the melted snow slides down the exterior surfaces of the inflatable portion to the ground, preventing snow from accumulating on the covered area, such as a driveway. In this way, safety is improved by preventing slippery driveway surfaces, and health risks are reduced by preventing the amount of strenuous activity required to clear snow from a driveway, sidewalk, or other snow-covered surface.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. An air mattress, comprising:
   an inflatable portion comprising a textile material;
   an outside air intake of the inflatable portion;
   a fan that draws outside air into the inflatable portion through the air intake, and circulates the air in the inflatable portion when inflated;
   an air divider that alternates between an inflating position that causes the fan to draw outside air into the inflatable portion and a circulating position that causes the fan to circulate air in the inflatable portion;
   an air heater that heats the air that passes through the fan;
   a heat sensor that senses the temperature of air in the inflatable portion;
   a pressure sensor that senses the air pressure in the inflatable portion;
   a snow sensor that senses contact with snow or ice; and
   a controller that:
      places the air divider in the inflating position and activates the fan and air heater based on a signal from the snow sensor;
      controls the divider based on a signal from the pressure sensor; and
      controls the heater based on a signal from the heat sensor.

2. The air mattress of claim 1, wherein the textile material comprises nylon.

3. The air mattress of claim 1, wherein the textile material comprises polyester.

4. The air mattress of claim 1, wherein the textile material is a ripstop textile.

5. The air mattress of claim 1, wherein the textile material comprises a hydrophobic coating.

6. The air mattress of claim 1, further comprising a plurality of air directing baffles disposed within the inflatable portion.

7. The air mattress of claim 1, further comprising a plurality of air directing tubes disposed within the inflatable portion.

8. The air mattress of claim 1, further comprising a plurality of support poles configured and disposed to support the inflatable portion.

9. The air mattress of claim 1, further comprising a plurality of tie downs affixed to edges of the air mattress proximate the surface on which the air mattress sits when inflated, the tie downs arranged to be attached to stakes protruding from the surface.

10. The air mattress of claim 9, further comprising a skirt panel arranged to cover the stakes when tied to the tie-downs.

11. The air mattress of claim 1, wherein the air heater comprises an electric heating element.

12. The air mattress of claim 1, wherein the air heater comprises a flammable gas heating element.

13. The air mattress of claim 1, further comprising a timer configured and disposed to deactivate the air heater after a predetermined time period.

14. The air mattress of claim 1, wherein the inflatable portion is configured to have a predetermined uniformly distributed average thickness when inflated.

15. The air mattress of claim 14, wherein the air mattress is configured when inflated to define a flat plane.

16. The air mattress of claim 14, wherein the air mattress is configured when inflated to define a tunnel having a front opening at a front end of the tunnel, and a rear opening at a rear end of the tunnel.

17. The air mattress of claim 16, further comprising a vibrator mechanism disposed to induce snow to slide off of the inflatable portion.

18. The air mattress of claim 16, further comprising a floor panel affixed to the tunnel portion.

19. The tent of claim 18, further comprising a strut affixed to and extending downward from the center of the top of the inflated tunnel, wherein the strut comprises a magnetic mount on a distal end of the strut.

20. The tent of claim 19, wherein the strut further includes a plurality of flexible straps mounted on the distal end of the strut.

* * * * *